US005591063A

United States Patent [19]
McCarthy

[11] Patent Number: 5,591,063
[45] Date of Patent: Jan. 7, 1997

[54] RAISED ORIENTATION PATTERN FOR NESTING BLOCKS FOR MEGACHILE ROTUNDATA

[75] Inventor: R. G. (Grant) McCarthy, St. Alberta, Canada

[73] Assignee: Beaver Plastics Limited, Edmonton, Canada

[21] Appl. No.: 364,652

[22] Filed: Dec. 27, 1994

[51] Int. Cl.[6] ........................................... A01K 47/00
[52] U.S. Cl. .................................................. 449/4
[58] Field of Search ................................ 449/4, 42, 43

[56] References Cited

U.S. PATENT DOCUMENTS

| | | |
|---|---|---|
| 3,267,497 | 8/1966 | Dority .................................. 449/4 |
| 3,936,894 | 2/1976 | Barber . | |
| 4,257,134 | 3/1981 | Niebur ................................ 449/4 X |
| 4,716,609 | 1/1988 | Norman .............................. 449/4 |
| 4,765,007 | 8/1988 | McCarthy . | |
| 4,787,108 | 11/1988 | Norman ............................ 449/1 |
| 5,403,226 | 4/1995 | Trafford ............................ 449/4 |

*Primary Examiner*—Robert P. Swiatek
*Attorney, Agent, or Firm*—Jones, Day, Reavis & Pogue

[57] ABSTRACT

In the raising and propagation of leaf cutter bees, rectangular nesting blocks molded from thermal plastics and having a number of open-ended apertures therethrough, are used. Each leaf cutter bee chooses one of the apertures in which to raise its sole progeny in the form of a larvae. In a typical leaf cutter bee nesting shelter, there may be several thousand apertures which appear to be identical. In order to orient the bee to its own aperture, the present invention uses a plurality of raised projections or portions on the front surface of the blocks to help the bees find their respective nesting apertures.

6 Claims, 3 Drawing Sheets

RAISED ORIENTATION PATTERN FOR NESTING BLOCKS FOR MEGACHILE ROTUNDATA

FIELD OF INVENTION

This invention relates to nesting blocks for bees and more particularly for megachile rotundata, commonly known as leaf cutter bees. Such bees are raised by alfalfa growers to pollinate and thus improve the crop.

BACKGROUND OF THE INVENTION

Leaf cutter bees are solitary bees and have long been known to improve pollination of alfalfa and like leguminosae pasture for seed. Leaf cutter bees, however, are not averse to living amongst their own kind. Each female constructs a cigar-like shaped cell inside blind tunnels or pre-existing holes.

In the prior art devices a plurality of laminated sheets or boards of wood having holes drilled therethrough, were used by managers of leaf cutter bee propagation stations. Nowadays, it is common to use rectangular blocks of molded thermal plastics having holes extending the entire thickness of the block at spaced apart intervals.

In a typical field shelter, the walls of such a shelter are lined with such blocks and the rear portion of the block is covered with a paper or some other similar substance to create closed ended tunnels.

Each bee shelter may contain as many as 20 or 25 such blocks and each block may contain up to 2500 tunnels or apertures for nesting.

Since all of the tunnels are identical in shape and form, there is often some difficulty for the bees to find their own particular nesting tunnel and progeny, amongst the many thousands of tunnels in the same shelter.

It has been found to be advantageous and of assistance to the bees to paint various forms of different colors and shapes with different colored backgrounds on the front face or entrance side of the blocks. It has been established that leaf cutter bees can recognize colors and geometric forms. It has thus long been the practice of farmers to use stencils to paint varying patterns on a background of different color on the face or entrance side of the blocks. This aids the bees in orienting themselves to their tunnels on return to the nest Typically, the forms may be a blue color on a black background. A typical stencil used for such painting is shown in U.S. Pat. No. 4,787,108, FIG. 7.

The problem with creating this type of orientation is that it is extremely time and labor consuming as each block must be painted by the farmer or keeper of the bees.

It is therefore an object of the present invention to create a block which is capable of orienting leaf cutter bees but which does not require painting by the farmer prior to use.

SUMMARY OF THE INVENTION

To the surprise of the inventor of the present invention, it has been found that leaf cutter bees are able to orient themselves to a block of a single color with a plurality of raised portions of varying geometrical shapes molded on the front face.

Therefore, this invention seeks to provide a nesting block for leaf cutter bees comprising a rectangular block constructed of moldable thermal plastics materials; said block having two ends, two sides, a front face and a rear face; said block including a plurality of open-ended parallel spaced apart nesting apertures; said apertures extending through the entire thickness of said block from said front face to said rear face, and being substantially perpendicular to said front and rear face; said rear and said front faces being substantially smooth and planar; the improvement being said front face includes a plurality of symmetrical or asymmetrical raised portions or projections on its surface; wherein, in field operation, said raised portions or projections serve to guide said bees to their respect nesting apertures.

The present invention is a great improvement over the painted orientation nesting blocks of the prior art. Raised geometrical forms can be incorporated onto the nesting block during the molding process for little or no cost. The raised portions can also be in the form of letters and numbers and identify the manufacturer and its trademark for the product. Such blocks, after molding, are immediately ready for the leaf cutter bee keeper to install in the field position without any painting or extra maintenance and labor.

BRIEF DESCRIPTION OF THE DRAWINGS

The invention will be described in greater detail in conjunction with the following drawings wherein.

DETAILED DESCRIPTION OF THE INVENTION

Figure 1:
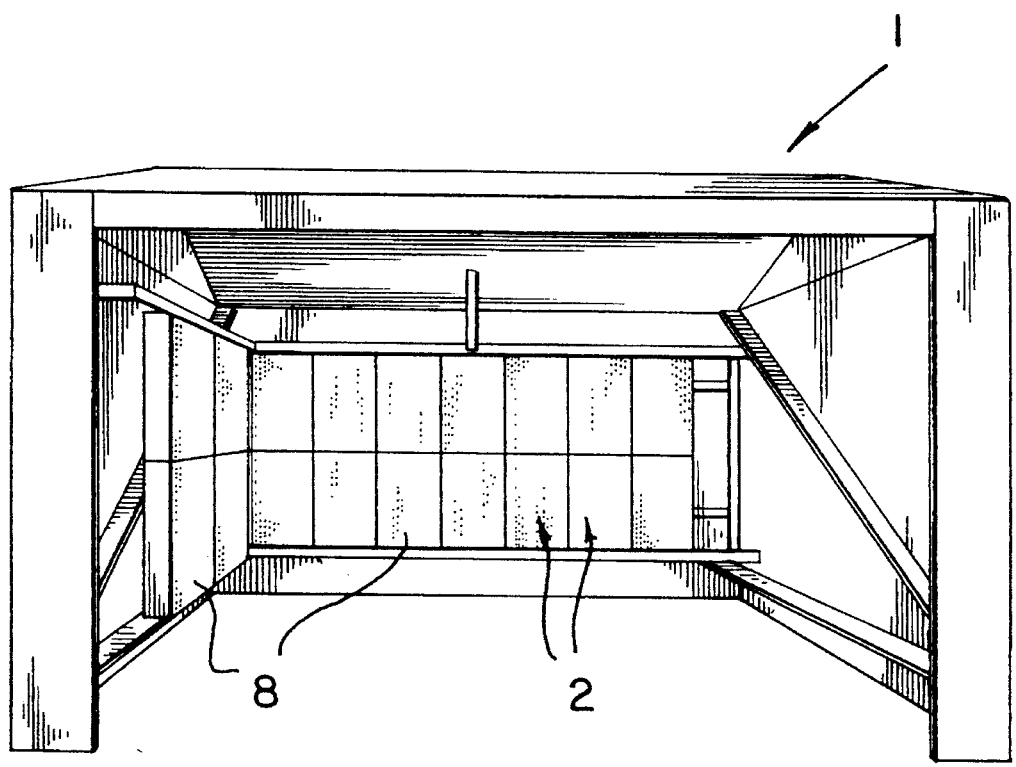
FIG. 1 is a perspective view of a typical present day field shelter for leaf cutter bee nesting blocks.

In FIG. 1, one sees a perspective view of a shed 1, which typically has a roof, sides, rear and an open front to permit the bees to enter and exit. It has a plurality of nesting blocks 2 lined against the walls with the front face or entry side 8 of the blocks 2 facing outward toward the open exit.

Figure 2:
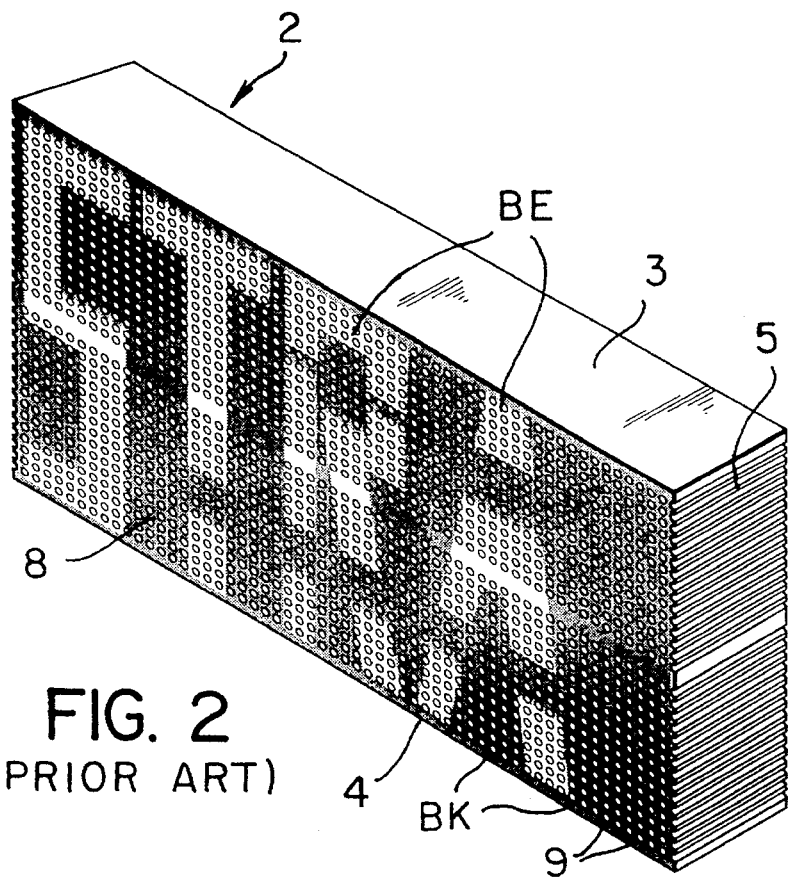
FIG. 2 is a perspective view of a prior art individual nesting block, showing the front face.
Figure 3:
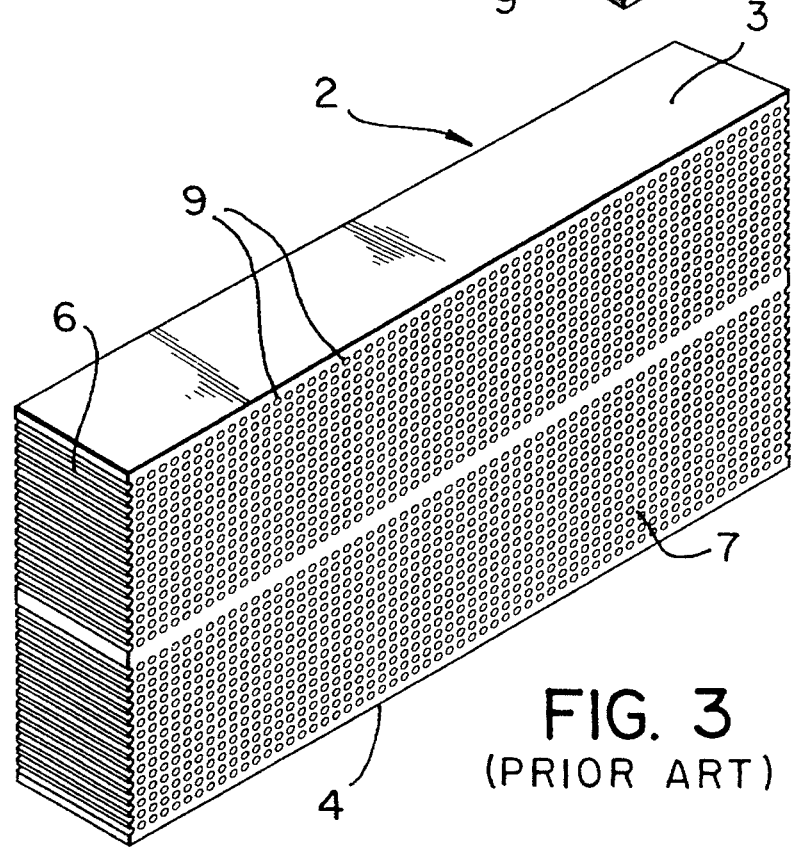
FIG. 3 is a perspective view of a prior art individual nesting block showing the rear face.

As seen more clearly in FIG. 2, the front face 8 of the blocks have been painted with a black background BK with various blue geometric shapes some of which are marked as BE. In FIGS. 2 and 3, the prior art blocks 2 have sides 3, 4, ends 5 and 6, a rear face 7 and a front face 8. One notes that the front 8 and rear 7 faces are substantially planar and identical. There are a plurality of open-ended apertures 9, which extend throughout the entire thickness of the block. In operation, the rear ends of the holes are blocked by waxed paper or some similar material such that the bees can enter only by the front face 8.

Figure 4:
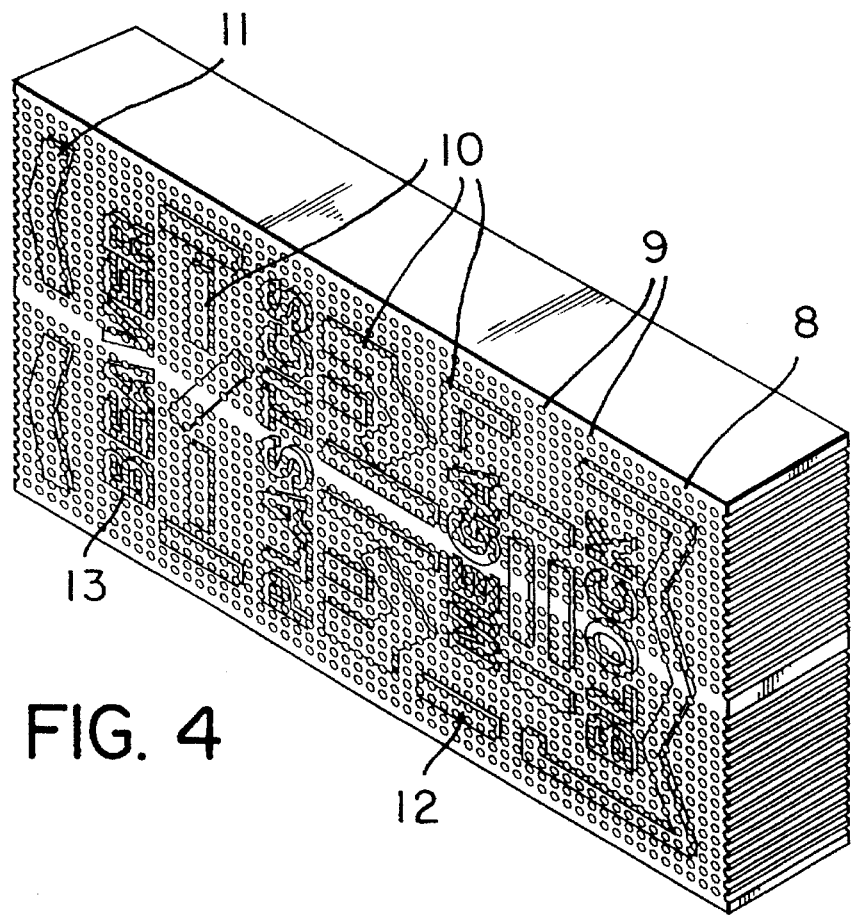
FIG. 4 is a perspective view of a nesting block of the present invention showing the entrance or front face.
Figure 5:
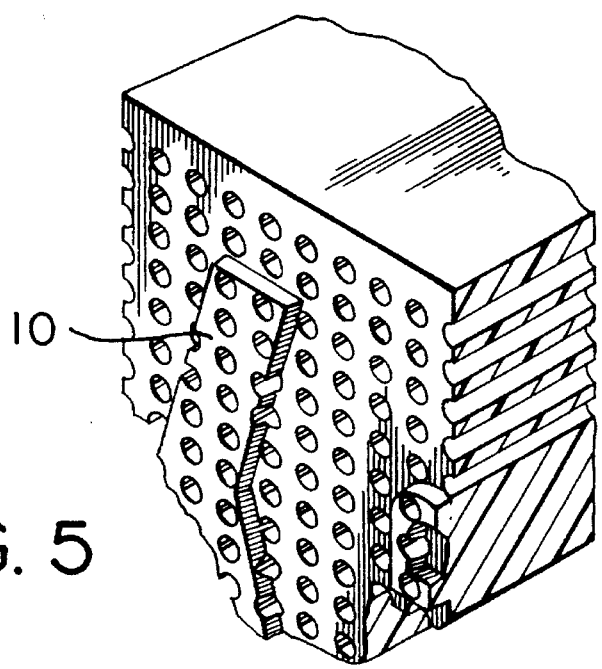
FIG. 5 is an expanded view of a portion of the nesting block of FIG. 4 illustrating a raised portion on the entrance or font face.

FIG. 4 is a perspective view of the block of the present invention. Looking towards the front face 8 one notes the apertures 9 and also a number of raised portions or projections 10. Such projections 10 extend outwardly from front face 8 generally about 1/16 of an inch from the otherwise substantially planar surface of the front face 8. The projections 10 of FIG. 4 have various configurations. For example, there are bars 11, rectangles 12 and even letters of the alphabet 13.

It has been found by the present inventor that such projections should extend at least 1/16 of an inch above the remainder of the front face portion. However, no particular height above that point appears to be better than any other. It has also been found that the raised portions or projections 10 may have various geometrical forms which are symmetrical or asymmetrical. The only requirement appears to be that there must be projections of different geometric configurations in any one proximity. Thus, a series of substantially identical parallel bar projections, spaced apart equidistantly, will not be as effective in orienting the bees, as a series of completely different asymmetric geometric forms of raised projections.

It is to be understood that any entrance or front face of a nesting block having one or more raised projections thereon, is contemplated by the present invention.

What I claim as my invention is:

1. A nesting block for leaf cutter bees comprising a rectangular block constructed of moldable thermal plastics material;
    said block having two ends, two sides, a front face and a rear face;
    said block including a plurality of open-ended parallel spaced apart nesting apertures;
    said apertures extending through the entire thickness of said block from said front face to said rear face, and being substantially perpendicular to said front and rear faces;
    said rear and said front faces being substantially smooth and planar;
    the improvement being said front face includes a plurality of asymmetrical raised portions or projections on its surface, said portions or projections being of different geometrical configurations;
    wherein, in field operation, said raised portions or projections serve to guide said bees to their respective nesting apertures.

2. A nesting block according to claim 1 wherein said portions or projections are of equal height and extend at least 1/16 of an inch above the remainder of the planar surface of said front face.

3. A nesting block according to claim 1 wherein said portions or projections of different geometrical configurations are created during a molding process.

4. A nesting block as claimed in claim 3 wherein said different geometrical configurations include letters of an alphabet.

5. A nesting block as claimed in claim 3 wherein said different geometrical configurations include numerals.

6. A method of orienting leaf cutter bees to a nesting site comprising the steps of:
    constructing a plurality of expanding polystyrene nesting blocks of equal dimension, with molded asymmetrical projections of varying geometrical configurations on one face of said blocks and placing said blocks in a shelter along the side and rear walls of said shelter with said one face of each of said blocks with said projections, facing outwardly towards an open central area of the shelter.

* * * * *